(12) United States Patent
Ishikawa et al.

(10) Patent No.: US 7,008,626 B2
(45) Date of Patent: Mar. 7, 2006

(54) MEDICAL COMPOSITION FOR PROTUBERANCE OF EPITHELIUM

(75) Inventors: Shin-ichi Ishikawa, Suginami-ku (JP); Junichi Onaya, Higashimurayama (JP)

(73) Assignee: Seikagaku Corporation, Tokyo (JP)

( * ) Notice: Subject to any disclaimer, the term of this patent is extended or adjusted under 35 U.S.C. 154(b) by 3 days.

(21) Appl. No.: 10/286,822

(22) Filed: Nov. 4, 2002

(65) Prior Publication Data

US 2003/0105061 A1 Jun. 5, 2003

(30) Foreign Application Priority Data

Nov. 5, 2001 (JP) .......................... P.2001-339471

(51) Int. Cl.
*A61K 7/00* (2006.01)
(52) U.S. Cl. ..................... 424/400; 424/422; 514/54; 514/62
(58) Field of Classification Search ............... 424/400, 424/422; 514/54, 62
See application file for complete search history.

(56) References Cited

U.S. PATENT DOCUMENTS 4,141,973 A * 2/1979 Balazs .................... 514/54
5,409,904 A * 4/1995 Hecht et al. ............. 514/23

FOREIGN PATENT DOCUMENTS

| JP | 2001-192336 A | 7/2001 |
| WO | WO 01/07056 A1 | 2/2001 |

OTHER PUBLICATIONS

Yamamoto et al., A Novel method of emdoscopic mucosal resection using sodium hyaluronate, 1999, Gastrointestinal Endoscopy, vol. 20, No. 2, pp 251-256.*

XP-009005857—H. Yamamoto et al., A Novel method of endoscopic mucosal resection using sodium hyaluronate, Gastrointestinal Endoscopy, (1999), vol. 50, No. 2, pp. 251-256.

XP-009005885—H. Yamamoto et al.. A successful single-step endoscolpic resection of a 40 millimeter flat-elevated tumor in the rectum: endoscopic mucosal resection using sodium hyaluronate, Gastrointestinal Endoscopy, (1999), vol. 50, No. 5, pp. 701-704.

* cited by examiner

*Primary Examiner*—Alton Pryor
*Assistant Examiner*—Konata M. George
(74) *Attorney, Agent, or Firm*—Sughrue Mion, PLLC

(57) ABSTRACT

A medical composition for protuberance of epithelium, which comprises a solution comprising a polysaccharide or a medically acceptable salt thereof, wherein the solution has a viscosity of: (1) from 50 to 500 mPa·s at a shear rate of from 7.7 to 10.0 $s^{-1}$; (2) from 45 to 300 mPa·s at a shear rate of from 19.2 to 20.0 $s^{-1}$; and (3) from 40 to 200 mPa·s at a shear rate of from 38.3 to 40.0 $s^{-1}$, when measured using a rotational viscometer at 25° C., and a syringe filled with the medical composition.

11 Claims, No Drawings

MEDICAL COMPOSITION FOR PROTUBERANCE OF EPITHELIUM

BACKGROUND OF THE PRESENT INVENTION

1. Field of the Invention

The present invention relates to a medical composition for protuberance of epithelium, which comprises a solution comprising a polysaccharide or a salt thereof, wherein the solution has predetermined properties. Also, the present invention relates to a syringe filled with the medical composition.

2. Brief Description of the Background Art

When it is necessary to apply a medical treatment to epithelium, e.g., when it is necessary to excise epithelium, the treatment can sometimes be facilitated by distending (elevating) the epithelium.

For example, endoscopic mucosal resection (hereinafter also referred to as "EMR") is a method in which mucosa, such as digestive tracts, changed into a morbid state is excised by an operation using an endoscope without ventrotomy, which is carried out by excising the region of mucosa changed into a morbid state by hooking the region with a wire loop attached to the tip of the endoscope. In order to improve efficiency, workability and safety of the operation, attempts have been made to develop a method for distending (elevating) a mucosa region changed into a morbid state by injecting a high molecular polymer solution into a lower layer of the mucosa region changed into a morbid state.

*Gastrointestinal Endoscopy*, 50(2), pp. 251–256 (1999) discloses that 1.0% sodium hyaluronate solution was used for elevation of mucosa in EMR, and discloses that it was administered using a disposable syringe.

Also, the same reference discloses that "a hypertonic saline and epinephrine" and "a hypertonic saline with epinephrine and 50% glucose" have been conventionally used for elevation of mucosa in EMR.

Furthermore, *Gastrointestinal Endoscopy*, 50(5), pp. 701–704 (1999) discloses that a 0.5% sodium hyaluronate solution containing a small amount of indigocarmine dye was used for elevation of mucosa in EMR, and that it was administered using a 5 ml capacity syringe.

Although EMR is an operation using an endoscope, a part of vital tissues must be removed and, when burden to patients is taken into consideration, it is preferable carry out the operation as quickly and securely as possible. Thus, great concern has been directed toward the development of a composition for quickly and securely carrying out medical treatments of epithelium, including the EMR.

SUMMARY OF THE INVENTION

An object of the present invention is to provide a composition for more quickly and securely carrying out medical treatments of epithelium, more particularly, a composition which can quickly carry out injection of a solution in treatment of epithelium, can keep high protuberance (elevation) of epithelium for a certain period of time, can exclude the necessity for additionally injecting a solution during the treatment of epithelium as small as possible, and can improve workability in treatment of epithelium.

Furthermore, an object of the present invention is to provide a syringe which is quickly used for the protuberance (elevation) of epithelium in treatment of epithelium.

These and other objects of the present invention have been accomplished by a medical composition for protuberance (elevation) of epithelium, which comprises a solution comprising a polysaccharide or a medically acceptable salt thereof, wherein the solution has a viscosity of:

(1) from 50 to 500 mPa·s at a shear rate of from 7.7 to 10.0 $s^{-1}$;

(2) from 45 to 300 mPa·s at a shear rate of from 19.2 to 20.0 $s^{-1}$; and (3) from 40 to 200 mPa·s at a shear rate of from 38.3 to 40.0 $0s^{-1}$, when measured using a rotational viscometer at 25° C. (hereinafter referred to as "composition of the present invention").

Furthermore, these and other objects of the present invention have been accomplished by a syringe filled with the composition of the present invention (hereinafter referred to as "syringe of the present invention").

Moreover, these and other objects of the present invention have been accomplished by a method for resecting epithelium, which comprises:

administering an effective amount of the medical composition to under epithelium to thereby obtain protuberance of the epithelium; and resecting the protuberance.

DETAILED DESCRIPTION OF THE INVENTION

As a result of intensive studies carried out in order to solve the above problems, the present inventors have found that when a solution having specified properties is used, the solution can be injected easily even through a thin catheter and needle and also high protuberance of epithelium can be kept for a certain period of time. Thus, the present invention has been completed.

It is preferable for the composition of the present invention that, in a syringe having a catheter needle and a piston which is filled with the solution, a force required for discharging the solution from the tip of the catheter needle by pushing the piston at a constant rate of 1 mm/second and at 25° C. is:

(1) 6.0 kgf or less when the catheter needle has a catheter length of 1,650 mm and a needle diameter of 21 G (gauge); and (2) 10.0 kgf or less when the catheter needle has a catheter length of 2,300 mm and a needle diameter of 25 G (gauge).

Furthermore, it is preferable in the composition of the present invention that, when 0.5 ml of the solution is injected under mucosa in the vicinity of a greater curvature pyloric portion of stomach of a rabbit from its gastric serosa side using an injection needle having a needle diameter of 27 G and subsequently allowed to stand for 30 minutes to obtain protuberance of the mucosa, and then a region comprising the protuberance is quickly frozen and vertically incised from the apex of the protuberance, the protuberance in the vertically incised section has a height of 5.0 mm or more from a mucosa surface of a region to which the solution is not injected.

The polysaccharide used in the composition of the present invention is preferably a glycosaminoglycan, and the glycosaminoglycan is preferably hyaluronic acid.

Also, when hyaluronic acid is used as the glycosaminoglycan, its weight average molecular weight (hereinafter referred to as "Mw") is preferably from 600,000 to 3,900, 000, more preferably from 700,000 to 3,000,000, and most preferably from 700,000 to 1,200,000 or from 1,900,000 to 3,000,000.

It is also preferable that the composition of the present invention further comprises chondroitin sulfate or a medically acceptable salt thereof. In this case, the ratio of the "hyaluronic acid or medically acceptable salt thereof" to the "chondroitin sulfate or medically acceptable salt thereof" is preferably from 1/10 to 1/20 (w/w (weight/weight)).

The epithelium having protuberance obtained by the composition of the present invention is preferably mucosa, and more preferably digestive organ mucosa. Also, it is preferable to use the composition of the present invention for a mucosal resection.

<1> Composition of the Present Invention

The composition of the present invention is a medical composition for protuberance of epithelium, which comprises a solution comprising a polysaccharide or a medically acceptable salt thereof, wherein the solution has a specific viscosity at each shear rate shown in Table 1 below, when measured using a rotational viscometer at 25° C.

TABLE 1

| Shear rate (s$^{-1}$) | Viscosity (mPa · s) |
|---|---|
| 7.7 to 10.0 | 50 to 500 |
| 19.2 to 20.0 | 45 to 300 |
| 38.3 to 40.0 | 40 to 200 |

(1) Polysaccharide or a Medically Acceptable Salt Thereof

The polysaccharide used in the composition of the present invention is not particularly limited, so long as it is suitable for medical use, and various polysaccharides can be used but a glycosaminoglycan is particularly preferable. Examples of the glycosaminoglycan include hyaluronic acid, chondroitin sulfate, keratan sulfate, heparin and heparan sulfate. Among these, hyaluronic acid is more preferred.

Also, examples of the medically acceptable salt of polysaccharide include medically acceptable salts selected from salts with inorganic bases such as alkali metal salts (e.g., sodium salts, lithium salts and potassium salts), alkaline earth metal salts (e.g., calcium salts and magnesium salts) and ammonium salt, and salts with organic bases such as diethanolamine salts, cyclohexylamine salts and amino acid salts. Among these, alkali metal salts are preferable, and sodium salts are more preferable.

The present invention is specifically described with reference to the case in which hyaluronic acid is used as the polysaccharide.

The origin of hyaluronic acid or a medically acceptable salt thereof used in this case is not particularly limited, and, e.g., those which are separated and purified from chicken crest, umbilical cords or hyaluronic acid-producing microorganisms can be used. Particularly preferred examples are those which are highly purified and have substantially no substances whose contamination is not allowed as a medicament. As the medically acceptable salt of hyaluronic acid, the salts described above can be used, and sodium hyaluronate is more preferable.

The Mw of hyaluronic acid or a medically acceptable salt thereof used in the present invention is not particularly limited, but is preferably shown in Table 2 below. The higher the No. in Table 2 is, the more preferable the range is.

TABLE 2

| No. | Mw |
|---|---|
| 1 | 600,000 to 3,900,000 |
| 2 | 700,000 to 3,000,000 |
| 3 | 700,000 to 1,200,000 or 1,900,000 to 3,000,000 |
| 4 | 800,000 to 1,000,000 or 1,900,000 to 2,500,000 |
| 5 | 850,000 to 950,000 or 2,000,000 to 2,400,000 |
| 6 | 880,000 to 920,000 or 2,100,000 to 2,300,000 |
| 7 | about 900,000 or about 2,200,000 |

Also, the Mw of hyaluronic acid or a medically acceptable salt thereof used in the present invention can be calculated based on the equation of Laurent et al. (*Biochem. Biophys. Acta*, 42, 476 (1960)) by measuring a limiting viscosity in accordance with *The Japanese Pharmacopoeia*, Thirteenth Edition, General Tests, "Viscosity Determination" (1996).

Additionally, the preferable relationship between the limiting viscosity of hyaluronic acid or a medically acceptable salt thereof and the Mw is shown in Table 3 below.

TABLE 3

| No. | Mw | Limiting viscosity (dl/g) |
|---|---|---|
| 1 | 600,000 to 3,900,000 | 11.5 to 54.5 |
| 2 | 700,000 to 3,000,000 | 13.0 to 44.0 |
| 3 | 700,000 to 1,200,000 | 13.0 to 20.0 |
|   | 1,900,000 to 3,000,000 | 30.0 to 44.0 |
| 4 | 800,000 to 1,000,000 | 14.5 to 17.0 |
|   | 1,900,000 to 2,500,000 | 30.0 to 38.0 |
| 5 | 850,000 to 950,000 | 15.0 to 16.5 |
|   | 2,000,000 to 2,400,000 | 31.5 to 36.5 |
| 6 | 880,000 to 920,000 | 15.5 to 16.0 |
|   | 2,100,000 to 2,300,000 | 33.0 to 35.5 |
| 7 | about 900,000 | about 16.0 |
|   | about 2,200,000 | about 34.0 |

Preferably, the composition of the present invention further comprises chondroitin sulfate or a medically acceptable salt thereof, in addition to hyaluronic acid or a medically acceptable salt thereof.

The origin of chondroitin sulfate or a medically acceptable salt thereof used in this case is not particularly limited, and, e.g., those which are separated and purified from cartilage of fishes (e.g., sharks) and mammals (e.g., whales and cattle) can be used. Particularly preferred examples are those which contain substantially no substances whose contamination is not allowed as a medicament. As the medically acceptable salt of chondroitin sulfate, the salts described above can be used, and sodium chondroitin sulfate is more preferable.

The Mw of chondroitin sulfate or a medically acceptable salt thereof used herein is generally from several thousands to about 50,000, preferably from about 10,000 to 40,000, and more preferably from about 20,000 to 30,000.

Particularly, sodium chondroitin sulfate having the following properties (1) and (2) is exceedingly preferable:
(1) the nitrogen content when a dried sample is determined is from 2.5 to 3.8%;
(2) the sulfur content when a dried sample is determined is from 5.5 to 7.5%.

Furthermore, the sodium chondroitin sulfate having the following properties (3) to (9) is more preferable:
(3) when 1.0 g of the sodium chondroitin sulfate is dissolved in 100 ml of water, the solution is colorless to slightly yellow transparent;
(4) the chloride content is 0.142% or less;
(5) the sulfate content is 0.24% or less;

(6) the heavy metal content is 20 ppm or less;

(7) the arsenic content is 2 ppm or less;

(8) the drying loss is 10.0% or less (1 g, 105° C., 4 hours);

(9) the ignition residue is from 23.0 to 31.0% (1 g, after drying).

Also, the properties (1) to (9) can be measured by the general tests described in *A Guide for The Japanese Pharmacopoeia, Thirteenth Edition* (published by Hirokawa Shoten) and the methods described in *The Japanese Medical Codex* (1997).

According to the composition of the present invention further comprising chondroitin sulfate or a medically acceptable salt thereof, in addition to hyaluronic acid or a medically acceptable salt thereof, the ratio of the "hyaluronic acid or medically acceptable salt thereof" to the "chondroitin sulfate or medically acceptable salt thereof" is preferably from 1/10 to 1/20 (w/w).

A solution comprising the polysaccharide or a medically acceptable salt thereof can be used as the solution comprising the composition of the present invention. The solution can be prepared by dissolving the polysaccharide or a medically acceptable salt thereof in an appropriate medically acceptable solvent. A kind of the solvent is not particularly limited, and sterilized distilled water or physiological salt solution can be used.

Among the solutions of polysaccharide or a medically acceptable salt thereof, a solution having the property shown in Table 1 above is used as the composition of the present invention.

As the rotational viscometer, a commercially available product can be used, and the shear rate can be adjusted by appropriately setting and selecting the rotation speed and type and size of the rotor (rotating device). Specific type and size of the rotor are not particularly limited, so long as they are generally used, and, e.g., a cone spindle type having "an angle of 1° 34' and a radius of 24 mm" or "an angle of 3° and a radius of 14 mm" can be used. The most preferable example is referred to Example described below.

Using such an instrument, a solution can be obtained used as the composition of the present invention, by appropriately adjusting a kind and an amount of the polysaccharide or a medically acceptable salt thereof and the solvent in such a manner that the solution shows each of the viscosity at each of the shear rate at 25° C.

A concentration of the polysaccharide or a medically acceptable salt thereof in the solution used as the composition of the present invention is not limited, so long as it has the property described in the above, and can be appropriately set in response to the kind, Mw and combination of the polysaccharide or a medically acceptable salt thereof. When two or more polysaccharides or medically acceptable salts thereof are used, it may be considered in the same manner on a solution in which they are mixed.

Furthermore, preferably, the solution used as the composition of the present invention further has the following property.

In a syringe having a catheter needle and a piston which is filled with the solution, a preferable range of a force required for discharging the solution from the tip of the catheter needle by pushing the piston at a constant rate of 1 mm/second at 25° C. is shown in Table 4 below. The higher the No. in Table 4 is, the more preferable the range is.

TABLE 4

| | Force | |
|---|---|---|
| No. | Catheter needle (1) Catheter length: 1,650 mm Needle diameter: 21 G | Catheter needle (2) Catheter length: 2,300 mm Needle diameter: 25 G |
| 1 | 6.0 kgf or less | 10.0 kgf or less |
| 2 | 6.0 kgf or less | 9.0 kgf or less |
| 3 | 5.0 kgf or less | 7.5 kgf or less |
| 4 | 5.0 kgf or less | 7.0 kgf or less |
| 5 | 4.0 kgf or less | 7.0 kgf or less |

The property can be measured by filling a syringe equipped with a catheter needle having the predetermined catheter length and needle diameter with the solution, and measuring a force required for discharging the solution from the tip of the catheter needle by pushing the piston at a constant rate of 1 mm/second. The measurement is carried out at 25° C. An inner diameter of the cylinder of the syringe (outer diameter of the piston under a state of being kept inside the cylinder) is set to about 14 mm. The most preferable example of the measuring method is referred to Example described below.

Furthermore, preferably, the composition of the present invention further has the following property.

When 0.5 ml of the solution is injected under mucosa in the vicinity of a greater curvature pyloric portion of stomach of a rabbit from its gastric serosa side using an injection needle having a needle diameter of 27 G and subsequently allowed to stand for 30 minutes to obtain protuberance of the mucosa, and then a region comprising the protuberance is quickly frozen and vertically incised from the apex of the protuberance, the protuberance in the vertically incised section has an average height of 5.0 mm or more, preferably 5.1 mm or more, and more preferably 5.2 mm or more, from a mucosa surface of a region to which the solution is not injected.

Since there is a possibility that an amount of the solution leaked from the region where the needle is inserted slightly differs depending on the needle diameter (thickness), the needle diameter of the needle was specified to 27 G in specifying the property in order to exclude influences caused thereby. Also, it is preferable to use dry ice for the quick freezing.

After the quick freezing, the administered region is vertically incised from the protuberance apex (vertical incision against the mucosa surface to which the solution is not administered). Next, using the mucosa surface in the section appeared by the vertical incision, to which the solution is not administered, as a standard, the height therefrom to the protuberance apex of the mucosa (mucosa surface being the protuberance apex) is measured. It is necessary to carry out a series of these operations while the frozen state is maintained, and since the measurement must be accurate and objective, it is preferable to measure the height by photographing the section appeared by the vertical incision and subjecting it to image analysis.

The evaluation of the height is preferably carried out using an average value based on plural tests. The tests are carried out, for example, about 4 times.

The most preferable example of the measuring method is referred to Example described below.

By using the solution comprising a polysaccharide or a medically acceptable salt thereof, the composition of the present invention which can perform easy solution injection and has good ability to keep protuberance of epithelium can be obtained.

Preferable examples of the solution comprising a polysaccharide or a medically acceptable salt thereof used in the composition of the present invention include:

(a) from 0.35 to 0.44% (w/v (weight/volume)) of sodium hyaluronate (Mw: from 700,000 to 1,200,000);

(b) from 0.15 to 0.34% (w/v) of sodium hyaluronate (Mw: from 1,900,000 to 3,000,000); and (c) a combination of from 0.05 to 0.24% (w/v) of sodium hyaluronate (Mw: from 1,900,000 to 3,000,000) with from 1.5 to 2.4% (w/v) of sodium chondroitin sulfate (Mw: from 20,000 to 30,000).

In the above solution (a), more preferable ranges are shown in Table 5 below. The higher the No. in Table 5 is, the more preferable the range is.

TABLE 5

| | Sodium hyaluronate | |
|---|---|---|
| No. | Mw | Concentration (w/v) |
| 1 | 800,000 to 1,000,000 | 0.35 to 0.44% |
| 2 | 850,000 to 950,000 | 0.35 to 0.44% |
| 3 | 850,000 to 950,000 | 0.38 to 0.42% |
| 4 | 880,000 to 920,000 | 0.38 to 0.42% |
| 5 | 880,000 to 920,000 | 0.4% |
| 6 | about 900,000 | 0.4% |

In the above solution (b), more preferable ranges are shown in Table 6 below. The higher the No. in Table 6 is, the more preferable the range is.

TABLE 6

| | Sodium hyaluronate | |
|---|---|---|
| No. | Mw | Concentration (w/v) |
| 1 | 1,900,000 to 2,500,000 | 0.15 to 0.34% |
| 2 | 2,000,000 to 2,400,000 | 0.15 to 0.34% |
| 3 | 2,100,000 to 2,300,000 | 0.15 to 0.34% |
| 4 | 2,100,000 to 2,300,000 | 0.18 to 0.32% |
| 5 | 2,150,000 to 2,250,000 | 0.18 to 0.32% |
| 6 | 2,150,000 to 2,250,000 | 0.2% or 0.3% |
| 7 | about 2,200,000 | 0.2% or 0.3% |

In the above solution (c), more preferable combinations and ranges are shown in Table 7 below. The higher the No. in Table 7 is, the more preferable the combination and range are.

TABLE 7

| | Sodium hyaluronate | | Sodium chondroitin sulfate | |
|---|---|---|---|---|
| No. | Mw | Conc. (w/v) | Mw | Conc. (w/v) |
| 1 | 1,900,000 to 2,500,000 | 0.05 to 0.24% | 20,000 to 30,000 | 1.5 to 2.4% |
| 2 | 2,000,000 to 2,400,000 | 0.05 to 0.24% | 20,000 to 30,000 | 1.5 to 2.4% |
| 3 | 2,100,000 to 2,300,000 | 0.05 to 0.24% | 20,000 to 30,000 | 1.5 to 2.4% |
| 4 | 2,100,000 to 2,300,000 | 0.08 to 0.22% | 20,000 to 30,000 | 1.5 to 2.4% |
| 5 | 2,150,000 to 2,250,000 | 0.08 to 0.22% | 20,000 to 30,000 | 1.5 to 2.4% |
| 6 | 2,150,000 to 2,250,000 | 0.08 to 0.22% | 20,000 to 30,000 | 1.8 to 2.2% |
| 7 | 2,150,000 to 2,250,000 | 0.1% or 0.2% | 20,000 to 30,000 | 1.8 to 2.2% |
| 8 | 2,150,000 to 2,250,000 | 0.1% or 0.2% | 20,000 to 30,000 | 2.0% |
| 9 | about 2,200,000 | 0.1% or 0.2% | 20,000 to 30,000 | 2.0% |

These are merely illustrations, and other examples can be employed as solutions used in the composition of the present invention, so long as they have the properties described in the above.

Also, the concentration of endotoxin in the composition of the present invention is preferably 0.25 EU/ml or less. The endotoxin concentration can be measured using an endotoxin measuring method well known and conventionally used by those skilled in the art, but the Limulus test method which uses horseshoe crab amoebocyte lysate components is preferable. Also, the EU (endotoxin unit) can be measured and calculated in accordance with the Japanese Industrial Standard, Biochemical Reagent Provisions (JIS K8008). Also, the iron content is preferably 20 ppm or less.

Also, the composition of the present invention preferably has a pH of from 3 to 10, more preferably from 4 to 10, still more preferably from 5 to 9, most preferably from 6 to 8, and far most preferably 6.8 to 7.8.

Moreover, the composition of the present invention preferably has an osmotic pressure ratio (a ratio to physiological saline) of from 0.7 to 1.4, more preferably from 0.8 to 1.3, and most preferably from 0.9 to 1.2.

Furthermore, other medicinally active components and components generally used in medicaments such as generally used stabilizers, emulsifiers, osmotic pressure controlling agents, buffer agents, tonicity agents, preservatives, soothing agents, coloring agents, fillers, binders, lubricants and disintegrating agents can be contained in the composition of the present invention, so long as they do not have bad influences on the polysaccharide or a medically acceptable salt thereof contained in the composition of the present invention, do not have influences on the effects of the present invention and have the properties as the composition of the present invention.

The epithelium distended by the composition of the present invention is not limited, so long as it is an epithelium whose protuberance is desired, and examples include skin and mucosa. Particularly, mucosa is preferable.

Mucosa includes digestive organ mucosa (e.g., oral mucosa and gastrointestinal mucosa), respiratory organ mucosa (e.g., nasal septum mucosa) and urogenital mucosa (e.g., bladder mucosa, vaginal mucosa and uterine mucosa). Among these, digestive organ mucosa is preferable.

Among the digestive organ mucosa, gastrointestinal mucosa is preferable. Examples of the gastrointestinal mucosa include esophageal mucosa, gastric mucosa, duodenal mucosa and large intestine mucosa.

The composition of the present invention is preferably used in mucosal resection. Regarding the mucosal resection, various operation methods are known in response to the regions where the mucosal resection is carried out and the tools and methods to be employed. Specifically, endoscopic mucosal resection (EMR), mucosal resection under a laparoscope, mucosal resection under a hysteroscope, transurethral bladder tumor resection and mucosal resection using a laser can be exemplified, and the composition of the present invention can be used in any one of these mucosal resections. Also, it is particularly preferable that the composition of the present invention is used in endoscopic mucosal resection (EMR) among these.

The composition of the present invention can be used by administering it under an epithelium region where protuberance of epithelium is required. When the composition of the present invention is administered under an epithelium, the administered composition of the present invention retains between the epithelium and muscle layer, and the epithelium is distended thereby. In order to prevent leaking of the administered composition of the present invention, the composition of the present invention is preferably administered by injection. Since medical treatment of epithelium becomes easy by distending the epithelium, epithelium treatment can be carried out more quickly and accurately.

A dose of the composition of the present invention is appropriately selected, depending on the object for treating epithelium, area of the epithelium to be treated and the administration method, without limitation, but roughly, 5 to 100 ml can be exemplified when used in human EMR.

Also, when the composition of the present invention is administered by injection, it can be used by filling it in a syringe at the clinical field, but the filling labor and risk of causing contamination at the field can be reduced by the use of the following syringe of the present invention.

<2> Syringe of the Present Invention

The syringe of the present invention is a drug-filled syringe in which the composition of the present invention is filled in advance. According to the syringe of the present invention, the composition of the present invention filled in the syringe is sealed with a piston, a plunger, a stopper or a cap, so that it can be distributed under conditions of being filled with the composition of the present invention. The syringe of the present invention can be produced by filling the composition of the present invention in a syringe.

The composition of the present invention filled in the syringe of the present invention is described above.

A material, shape and size of the syringe filled with the composition of the present invention are not particularly limited, and those which are already known can be employed.

Furthermore, the method for filling the composition of the present invention in the syringe is also not particularly limited, and a known method can be employed.

When the syringe of the present invention is used, the labor for filling the composition of the present invention in a syringe and risk of causing contamination at the clinical field can be reduced.

The composition of the present invention can be injected quickly and easily as a solution even through thin catheter and needle and can keep a high protuberance of epithelium during its treatment. Thus, the composition of the present invention contributes to easier treatment of the epithelium as a vital tissue and to the shortening of the treating period. Also, since a necessity for additionally injecting a solution during the treatment can be reduced, the treatment can be carried out more safely and accurately. Accordingly, the composition of the present invention leads to the alleviation of burden on a patient who is subjected to a treatment of epithelium and therefore is markedly useful.

Furthermore, the syringe of the present invention is markedly useful, because it is already filled with the composition of the present invention, so that labor for the filling and risk of causing contamination at the clinical field can be reduced.

The present invention is described in more detail based on Example; however, the present invention is not limited thereto.

EXAMPLE

1. Substances to Be Tested (1) Sodium Hyaluronate

The following sodium hyaluronate samples were used as the medically acceptable salt of hyaluronic acid:

(a) Mw: 900,000, limiting viscosity: 15.9 dl/g (hereinafter referred to as "HA90");

(b) Mw: 2,200,000, limiting viscosity: 34.0 dl/g (hereinafter referred to as "HA220");

(c) a commercially available sodium hyaluronate intraarticular injection (trade name: Suvenyl®, available from Chugai Pharmaceutical, average molecular weight: 1,900,000 to 2,500,000) (hereinafter referred to as "HA-S"); and (d) a commercially available sodium hyaluronate agent (trade name: Healon®, available from Pharmacia, average molecular weight: 1,900,000 to 3,900,000) (hereinafter referred to as "HA-H").

(2) Sodium Chondroitin Sulfate

As the medically acceptable salt of chondroitin sulfate, sodium chondroitin sulfate (hereinafter referred to as "CS") prepared by extracting a shark cartilage by treating it with a protease in the usual way, subjecting the extract to a deproteinization using a protease after removing fat and solid contents and then purifying it by an alcohol precipitation method was used.

The Mw of the CS was 30,000, and its dried product (powder) showed the following properties:

(1) the nitrogen content: 3.40%;

(2) the sulfur content: 6.82%;

(3) color of liquid when 1.0 g of the compound is dissolved in 100 ml of water: colorless to slightly yellow transparent;

(4) the chloride content: 0.142% or less;

(5) the sulfate content: 0.24% or less;

(6) the heavy metal content: 20 ppm or less;

(7) the arsenic content: 2 ppm or less;

(8) the drying loss: 5.67% (1 g, 105° C., 4 hours); and (9) the ignition residue: 26.3% (1 g, after drying).

2. Preparation of Various Solutions and Viscosity

Solutions were prepared by dissolving the HA90, HA220, HA-S, HA-H and CS in physiological saline to give the following composition concentration (% (w/v)). Also, the viscosity (mPa·s) of each of these solutions at the following shear rate was measured at 25° C. using an RE80L type rotational viscometer and a cone spindle type rotor (angle: 1° 34'; radius: 24 mm) (manufactured by Toki Sangyo Co., Ltd.). The results are shown in Tables 8 and 9 below. In this case, * shows that it is an example of the composition of the present invention, and "ND" means that the measurement was not carried out.

TABLE 8

|  | Shear rate | | |
| --- | --- | --- | --- |
|  | 7.7 s$^{-1}$ | 19.2 s$^{-1}$ | 38.3 s$^{-1}$ |
| (1) Physiological saline | ND | ND | ND |
| (2) 0.1% HA220 | ND | 18.7 | 16.1 |
| (3) 0.2% HA220 * | 134.7 | 93.7 | ND |
| (4) 0.3% HA220 * | ND | ND | ND |
| (5) 0.4% HA90 * | 52.2 | 50.6 | 47.6 |
| (6) 0.5% HA90 | 94.3 | 88.9 | ND |
| (7) 0.2% HA-S * | ND | ND | ND |
| (8) 0.25% HA-S * | ND | ND | ND |
| (9) 0.3% HA-S * | ND | ND | ND |
| (10) 0.2% HA-H * | ND | ND | ND |
| (11) 0.25% HA-H * | ND | ND | ND |
| (12) 0.3% HA-H * | ND | ND | ND |
| (13) 2.0% CS | ND | ND | 7.4 |
| (14) 3.0% CS | ND | 13.8 | 13.6 |
| (15) 4.0% CS | ND | 24.8 | 24.8 |
| (16) 5.0% CS | 41.1 | 40.7 | 40.7 |
| (17) 2.0% CS + 0.05% HA220 | 22.2 | 20.2 | 19.0 |
| (18) 2.0% CS + 0.1% HA220 * | 58.8 | 49.2 | 41.8 |
| (19) 2.0% CS + 0.2% HA220 * | ND | ND | ND |
| (20) 3.0% CS + 0.05% HA220 | 36.9 | 34.4 | 32.3 |

TABLE 9

|  | Shear rate | |
| --- | --- | --- |
|  | 1.9 s$^{-1}$ | 3.8 s$^{-1}$ |
| (19) 2.0% CS + 0.2% HA220 * | 397.2 | 243.3 |

Also, the viscosity (mPa·s) of each of the following solutions at the following shear rate was measured under the same conditions, except that a cone spindle type rotor (angle: 30; radius: 14 mm) (manufactured by Toki Sangyo Co., Ltd.) was used as the rotor. The results are shown in Table 10 below.

TABLE 10

|  | Shear rate | | |
| --- | --- | --- | --- |
|  | 8.0 s$^{-1}$ | 20.0 s$^{-1}$ | 40.0 s$^{-1}$ |
| (3) 0.2% HA220 * | ND | 94.9 | 68.1 |
| (4) 0.3% HA220 * | 323.8 | 205.1 | 137.1 |
| (5) 0.4% HA90 * | ND | 61.1 | 57.6 |
| (6) 0.5% HA90 | ND | 132.2 | 117.4 |
| (7) 0.2% HA-S * | ND | 68.6 | 54.5 |
| (8) 0.25% HA-S * | 177.3 | 132.2 | 98.5 |
| (9) 0.3% HA-S * | 306.2 | 215.3 | 152.3 |
| (10) 0.2% HA-H * | 163.6 | 109.6 | 77.5 |
| (11) 0.25% HA-H * | 280.8 | 175.2 | 117.2 |
| (12) 0.3% HA-H * | 465.9 | 274.6 | 177.1 |

It was found from the above results that (3) 0.2% HA220, (4) 0.3% HA220, (5) 0.4% HA90, (6) 0.5% HA90, (7) 0.2% HA-S, (8) 0.25% HA-S, (9) 0.3% HA-S, (10) 0.2% HA-H, (11) 0.25% HA-H, (12) 0.3% HA-H, (18) 2.0% CS+0.1% HA220 and (19) 2.0% CS+0.2% HA220 satisfied the following conditions shown in Table 11, but the other solutions did not satisfied them.

TABLE 11

| Shear rate (s$^{-1}$) | Viscosity (mPa·s) |
| --- | --- |
| 7.7 to 10.0 | 50 to 500 |
| 19.2 to 20.0 | 45 to 300 |
| 38.3 to 40.0 | 40 to 200 |

Also, the measurement was not carried out regarding the "ND", and the measurement was not carried out at the predetermined shear rate particularly on (19) 2.0% CS+0.2% HA220, but whether or not they satisfy the above conditions can be easily judged by those skilled in the art when the results at other shear rate are compared with the technical common knowledge in the technical field.

When the endotoxin concentration in these solutions was measured using Toxi Color (trade name; manufactured by Seikagaku Corporation), it was 0.25 EU/ml or less in all of them. Also, the iron content was 20 ppm or less in all of them.

Furthermore, the pH of these solutions was within the range of from 6.8 to 7.8, and the osmotic pressure ratio (ratio to physiological saline) was within the range of from 0.9 to 1.2.

3. Discharging Force from Needle

Also, a syringe (inner diameter of the cylinder: 14 mm) equipped with the following catheter needle was filled with each of these solutions, and a force required for discharging the solution from the tip of a catheter needle when a piston of the syringe was pushed at a constant rate of 1 mm/second was measured under a condition of 25° C. using a rheometer (trade name: FUDOH Rheometer NRM-2020J Type, manufactured by Rheotech).

(1) Catheter length: 1,650 mm, needle diameter: 21 G (product name: Disposable Needle NM NM-200L-0421, manufactured by Olympus; hereinafter also referred to as "Catheter 1")

(2) Catheter length: 2,300 mm, needle diameter: 25 G (product name: Disposable Needle NM NM-200U-0625, manufactured by Olympus; hereinafter also referred to as "Catheter 2")

The results obtained by calculating average values by measuring 1 to 3 times for each sample are shown in Table 12 below as "average value±standard deviation (kgf)". In this case, * shows that it is an example of the composition of the present invention, and "ND" means that the measurement was not carried out.

TABLE 12

|  | Catheter 1 | Catheter 2 |
| --- | --- | --- |
| (1) Physiological saline | 0.4 ± 0.05 | 0.7 ± 0.07 |
| (2) 0.1% HA220 | 1.3 ± 0.04 | 2.4 ± 0.00 |
| (3) 0.2% HA220 * | 2.6 ± 0.06 | 4.3 ± 0.16 |
| (4) 0.3% HA220 * | 3.8 ± 0.00 | 6.4 ± 0.00 |
| (5) 0.4% HA90 * | 4.5 ± 0.00 | 6.9 ± 0.29 |
| (6) 0.5% HA90 | 6.5 ± 0.00 | 9.6 ± 0.58 |
| (13) 2.0% CS | 1.9 ± 0.01 | 4.2 ± 0.07 |
| (14) 3.0% CS | 3.6 ± 0.13 | 7.5 ± 0.09 |
| (15) 4.0% CS | 6.3 ± 0.24 | 12.8 ± 0.30 |
| (16) 5.0% CS | 10.0 ± 0.30 | 19.2 ± 0.73 |
| (17) 2.0% CS + 0.05% HA220 | 2.9 ± 0.10 | 6.0 ± 0.08 |
| (18) 2.0% CS + 0.1% HA220 * | 3.9 ± 0.08 | 7.1 ± 0.00 |
| (19) 2.0% CS + 0.2% HA220 * | 5.6 ± 0.13 | 9.6 ± 0.00 |
| (20) 3.0% CS + 0.05% HA220 | 5.0 ± 0.07 | 9.8 ± 0.28 |

4. Action to Maintain Protuberance (Elevation) of Epithelium

Under inhalation anesthesia of isoflurane (manufactured by Dainippon Pharmaceutical), 0.5 ml of the solution was administered under the mucosa in the vicinity of a greater curvature pyloric portion of stomach of a rabbit of female JW species having a body weight of from 2.60 to 3.43 kg, from the gastric serosa side using a needle having a needle diameter of 27 G. After 30 minutes of standing, the stomach was excised, and the administered region was quickly frozen with dry ice and then vertically incised from the protuberance apex on the administered region (vertical incision against the mucosa surface to which the solution was not administered). The section appeared by the vertical incision under frozen state was photographed, and using the mucosa surface of the region to which the solution was not administered as a standard, the height therefrom to the protuberance apex of the mucosa (mucosa surface being the protuberance apex) was measured using an image analyzing software (Image pro Plus™, manufactured by Media Cybernetics). The results are shown in Table 13 below as "average value±standard deviation (mm) (4 sites for 1 group)". In this case, * shows that it is an example of the composition of the present invention.

TABLE 13

| | | |
|---|---|---|
| (1) | Physiological saline | 3.8 ± 0.6 |
| (2) | 0.1% HA220 | 4.8 ± 1.0 |
| (3) | 0.2% HA220 * | 5.1 ± 0.4 |
| (4) | 0.3% HA220 * | 5.0 ± 0.5 |
| (5) | 0.4% HA90 * | 5.2 ± 0.4 |
| (6) | 0.5% HA90 | 5.0 ± 0.4 |
| (13) | 2.0% CS | 4.2 ± 0.8 |
| (14) | 3.0% CS | 4.4 ± 0.5 |
| (15) | 4.0% CS | 5.0 ± 0.6 |
| (16) | 5.0% CS | 4.8 ± 0.8 |
| (17) | 2.0% CS + 0.05% HA220 | 4.7 ± 0.3 |
| (18) | 2.0% CS + 0.1% HA220 * | 5.6 ± 1.0 |
| (19) | 2.0% CS + 0.2% HA220 * | 5.3 ± 0.5 |
| (20) | 3.0% CS + 0.05% HA220 | 4.9 ± 0.5 |

It was found from the above results that the use of a polysaccharide solution having the following property renders possible provision of a composition which facilitates its easy administration due to reduced discharging force when the solution is injected through thin catheter and needle using a syringe (it is 6.0 kgf or less when the catheter length is 1,650 mm and the needle diameter is 21 G, and it is 10.0 kgf or less when the catheter length is 2,300 mm and the needle diameter is 25 G) and which also can keep protuberance of epithelium at such a height that treatment of the epithelium can be easily carried out (average 5.0 mm or more) for a certain period of time (30 minutes).

When measured using a rotational viscometer under a condition of 25° C., its viscosity at the following shear rate is shown in Table 14 below.

TABLE 14

| Shear rate ($s^{-1}$) | Viscosity (mPa · s) |
|---|---|
| 7.7 to 10.0 | 50 to 500 |
| 19.2 to 20.0 | 45 to 300 |
| 38.3 to 40.0 | 40 to 200 |

While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application No. 2001-339471 filed on Nov. 5, 2001, the entire contents of which are incorporated hereinto by reference.

What is claimed is:

1. A method for resecting epithelium, which comprises:
    administering an effective amount of a medical composition to under epithelium to thereby obtain protuberance of the epithelium; and
    resecting the protuberance, wherein the medical composition comprises a solution consisting essentially of hyaluronic acid or a medically acceptable salt thereof and chondroitin sulfate or a medically acceptable salt thereof wherein the medical composition has a viscosity of:
    (1) from 50 to 500 mPa·s at a shear rate of from 7.7 to 10.0 $s^{-1}$;
    (2) from 45 to 300 mPa·s at a shear rate of from 19.2 to 20.0 $s^{-1}$; and
    (3) from 40 to 200 mPa·s at a shear rate of from 38.3 to 40.0 $s^{-1}$,
    when measured using a rotational viscometer at 25° C., chondroitin sulfate or a medically acceptable salt thereof.

2. The method according to claim 1, wherein the epithelium is mucosa.

3. The method according to claim 1, wherein, in a syringe having a catheter needle and a piston which is filled with the medical composition comprises applying a force required for discharging the medical composition from the tip of the catheter needle by pushing the piston at a constant rate of 1 mm/second and at 25° C. is, wherein said force:
    (1) 6.0 kgf or less when the catheter needle has a catheter length of 1,650 mm and a needle diameter of 21 G; and
    (2) 10.0 kgf or less when the catheter needle has a catheter length of 2,300 mm and a needle diameter of 25 G.

4. The method according to claim 1, wherein, when 0.5 ml of the medical composition is injected under mucosa in the vicinity of a greater curvature pyloric portion of stomach of a rabbit from its gastric serosa side using an injection needle having a needle diameter of 27 G and subsequently allowed to stand for 30 minutes to obtain protuberance of the mucosa, and then a region comprising the protuberance is quickly frozen and vertically incised from the apex of the protuberance, the protuberance in the vertically incised section has an average height of 5.0 mm or more from a mucosa surface of a region to which the medical composition is not injected.

5. The method according to claim 1, wherein the hyaluronic acid has a weight average molecular weight of from 600,000 to 3,900,000.

6. The method according to claim 1, wherein the hyaluronic acid has a weight average molecular weight of from 700,000 to 3,000,000.

7. The method according to claim 1, wherein the hyaluronic acid has a weight average molecular weight of from 700,000 to 1,200,000 or from 1,900,000 to 3,000,000.

8. The method according to claim 1, wherein the ratio of the hyaluronic acid or medically acceptable salt thereof to the chondroitin sulfate or medically acceptable salt thereof is from 1/10 to 1/20 (w/w).

9. The method according to claim 2, wherein the mucosa is digestive organ mucosa.

10. The method according to claim 1, which is used for a mucosal resection.

11. The method according to claim 1, wherein the composition is stored in a syringe prior to use.

* * * * *